United States Patent
Park et al.

(10) Patent No.: US 12,150,790 B2
(45) Date of Patent: Nov. 26, 2024

(54) METHOD OF OBTAINING FEATURE FOR BLOOD PRESSURE ESTIMATION, APPARATUS AND METHOD FOR ESTIMATING BLOOD PRESSURE

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Young Soo Kim, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 484 days.

(21) Appl. No.: 17/489,130

(22) Filed: Sep. 29, 2021

(65) Prior Publication Data

US 2022/0265220 A1 Aug. 25, 2022

(30) Foreign Application Priority Data

Feb. 19, 2021 (KR) ......................... 10-2021-0022413

(51) Int. Cl.
*A61B 5/00* (2006.01)
*A61B 5/021* (2006.01)
(Continued)

(52) U.S. Cl.
CPC ........ *A61B 5/7278* (2013.01); *A61B 5/02116* (2013.01); *A61B 5/02125* (2013.01);
(Continued)

(58) Field of Classification Search
CPC ... A61B 5/7278; A61B 5/02116; A61B 5/024; A61B 5/7239; A61B 5/02108; A61B 5/7275
See application file for complete search history.

(56) References Cited

U.S. PATENT DOCUMENTS 9,546,898 B2 1/2017 Kovacs
9,549,680 B2 1/2017 Giovangrandi et al.
(Continued)

FOREIGN PATENT DOCUMENTS

JP 2017-517373 A 6/2017
KR 10-2013-0024379 A 3/2013
(Continued)

OTHER PUBLICATIONS

Yoon et al., "Nonconstrained Blood Pressure Measurement by Photoplethysmography", Journal of the Optical Society of Korea, vol. 10, No. 2, Jun. 2006, 5 pages total.
(Continued)

*Primary Examiner* — Eric F Winakur
*Assistant Examiner* — Jaimie Annette McKeel
(74) *Attorney, Agent, or Firm* — Sughrue Mion, PLLC

(57) ABSTRACT

A method of obtaining a feature for blood pressure estimation is provided. The method includes extracting a reference feature from a bio-signal; obtaining a feature for blood pressure estimation by: obtaining, as the feature for blood pressure estimation, a first candidate feature based on the reference feature being less than a first threshold; obtaining, as the feature for blood pressure estimation, a second candidate feature based on the reference feature being greater than or equal to a second threshold that is greater than the first threshold; or obtaining, as the feature for blood pressure estimation, a combination of the first candidate feature and the second candidate feature based on the reference feature being less than the second threshold; and estimating a blood pressure by using the obtained feature.

20 Claims, 12 Drawing Sheets

(51) Int. Cl.
*A61B 5/024* (2006.01)
*A61B 5/029* (2006.01)

(52) U.S. Cl.
CPC .............. *A61B 5/024* (2013.01); *A61B 5/029* (2013.01); *A61B 5/7239* (2013.01); *A61B 2560/0223* (2013.01)

(56) References Cited

U.S. PATENT DOCUMENTS

| | | |
|---|---|---|
| 9,568,354 B2 | 2/2017 | Kovacs et al. |
| 9,943,241 B2 | 4/2018 | Giovangrandi et al. |
| 9,949,662 B2 | 4/2018 | Giovangrandi et al. |
| 10,130,273 B2 | 11/2018 | Kovacs et al. |
| 10,426,411 B2 | 10/2019 | Li |
| 10,451,473 B2 | 10/2019 | Kovacs |
| 2002/0007114 A1 | 1/2002 | Elghazzawi |
| 2015/0032382 A1 | 1/2015 | Lee et al. |
| 2015/0342478 A1 | 12/2015 | Galen et al. |
| 2016/0022156 A1 | 1/2016 | Kovacs et al. |
| 2016/0249820 A1 | 9/2016 | Puig et al. |
| 2016/0270668 A1 | 9/2016 | Gil |
| 2017/0211968 A1 | 7/2017 | Kovacs et al. |
| 2018/0177466 A1* | 6/2018 | Park .................. A61B 5/389 |
| 2019/0038185 A1 | 2/2019 | Arnold et al. |
| 2019/0110757 A1 | 4/2019 | Kwon et al. |
| 2019/0254610 A1 | 8/2019 | Park et al. |
| 2020/0113453 A1 | 4/2020 | Park et al. |
| 2020/0113526 A1 | 4/2020 | Park et al. |
| 2021/0007615 A1 | 1/2021 | Jang et al. |
| 2022/0313098 A1* | 10/2022 | LeBoeuf .............. A61B 5/7264 |

FOREIGN PATENT DOCUMENTS

| | | |
|---|---|---|
| KR | 10-2015-0012104 A | 2/2015 |
| KR | 10-1503604 B1 | 3/2015 |
| KR | 10-2018-0002524 A | 1/2018 |
| KR | 10-2018-0042719 A | 4/2018 |
| KR | 10-2019-0043453 A | 4/2019 |
| KR | 10-2019-0100020 A | 8/2019 |
| KR | 10-2020-0040563 A | 4/2020 |
| KR | 10-2020-0041680 A | 4/2020 |
| KR | 10-2021-0007368 A | 1/2021 |

OTHER PUBLICATIONS

Millasseau et al., "The Vascular Impact of Aging and Vasoactive Drugs: Comparison of Two Digital Volume Pulse Measurements", The American Journal of Hypertension, Ltd., vol. 16, No. 6, 2003, 6 pages total.

Baruch et al., "Validation of the pulse decomposition analysis algorithm using central arterial blood pressure", BioMedical Engineering OnLine, 2014, 19 pages total.

Communication dated Apr. 4, 2023 by the Korean Intellectual Property Office in Korean Application No. 10-2021-0022413.

* cited by examiner

METHOD OF OBTAINING FEATURE FOR BLOOD PRESSURE ESTIMATION, APPARATUS AND METHOD FOR ESTIMATING BLOOD PRESSURE

CROSS-REFERENCE TO RELATED APPLICATION(S)

This application claims priority to Korean Patent Application No. 10-2021-0022413, filed on Feb. 19, 2021, in the Korean Intellectual Property Office, the entire disclosure of which is herein incorporated by reference for all purposes.

BACKGROUND

1. Field

Example embodiments of the present disclosure relate to an apparatus and a method for non-invasively estimating blood pressure, and to a technique of obtaining a feature for blood pressure estimation.

2. Description of Related Art

With the aging population, increased medical costs, and insufficient medical personnel for specialized medical services, research is being conducted on information technology (IT)-medical convergence technologies, in which IT technology and medical technology are combined. Particularly, monitoring of a health condition of a human body may not be limited to places such as hospitals, but is expanded by mobile healthcare fields that may monitor a user's health condition anywhere (e.g., at home or office on in transit from one place to another place) and anytime in daily life. Some examples of bio-signals, which indicate the health condition of individuals, may include an electrocardiography (ECG) signal, a photoplethysmogram (PPG) signal, an electromyography (EMG) signal, and the like, and various bio-signal sensors are being developed to measure the bio-signals in daily life. For example, the PPG sensor may estimate blood pressure of a human body by analyzing a pulse waveform which reflects a condition of the cardiovascular system and the like, wherein a PPG signal is based on a superposition of a propagation wave starting from the heart toward the body distal ends and reflection waves returning from the body distal ends.

SUMMARY

According to an aspect of an example embodiment, there is provided a method of obtaining a feature for blood pressure estimation, the method including: extracting a reference feature from a bio-signal; obtaining a feature for blood pressure estimation by: obtaining, as the feature for blood pressure estimation, a first candidate feature based on the reference feature being less than a first threshold; obtaining, as the feature for blood pressure estimation, a second candidate feature based on the reference feature being greater than or equal to a second threshold that is greater than the first threshold; or obtaining, as the feature for blood pressure estimation, a combination of the first candidate feature and the second candidate feature based on the reference feature being less than the second threshold; and estimating a blood pressure by using the obtained feature.

The reference feature may include at least one of a heart rate, a feature associated with the heart rate, a value obtained by normalizing the heart rate to a heart rate obtained at a time of calibration, or a value obtained by normalizing the feature associated with the heart rate to a feature associated with the heart rate obtained at the time of calibration.

The first candidate feature may include a ratio between an amplitude of a reflection wave component in the bio-signal and an amplitude of a predetermined point in a systolic interval.

The predetermined point in the systolic interval may include at least one of a maximum amplitude point and a point obtained by internally dividing a time of a propagation wave component and a time of the maximum amplitude point.

The second candidate feature may include a ratio of an amplitude of a reflection wave component and an amplitude of a propagation wave component in the bio-signal.

The method may further include, prior to extracting the reference feature, extracting the first candidate feature and the second candidate feature based on the bio-signal.

The extracting the first candidate feature and the second candidate feature may include acquiring a second-order differential signal of the bio-signal and extracting the first candidate feature and the second candidate feature based on a local minimum point of the acquired second-order differential signal.

The method may further include: extracting the first candidate feature from the bio-signal, based on the reference feature being less than the first threshold; extracting the second candidate feature from the bio-signal, based on the reference feature being greater than or equal to the second threshold; and extracting the first candidate feature and the second candidate feature from the bio-signal, based on the reference feature being less than the second threshold.

The obtaining the feature for blood pressure estimation based on the combination of the first candidate feature and the second candidate feature may include obtaining the feature for blood pressure estimation through a linear combination or a non-linear combination of the first candidate feature and the second candidate feature.

According to an aspect of an example embodiment, there is provided an apparatus for estimating blood pressure, including: a sensor configured to acquire a bio-signal from an object; and a processor configured to: extract a reference feature based on the bio-signal; obtain, as a feature for blood pressure estimation, a first candidate feature based on the reference feature being less than a first threshold, a second candidate feature based on the reference feature being greater than or equal to a second threshold that is greater than the first threshold, or a combination of the first candidate feature and the second candidate feature based on the reference feature being greater than or equal to the first threshold and less than the second threshold; and estimate a blood pressure by using the obtained feature.

The feature for blood pressure estimation may include a cardiac output (CO)-associated feature and a total peripheral resistance (TPR)-associated feature.

The CO-associated feature may include at least one of a heart rate, a maximum amplitude of a systolic period, or an area of a bio-signal waveform.

The reference feature may include at least one of a heart rate, a feature associated with the heart rate, a value obtained by normalizing the heart rate to a heart rate obtained at a time of calibration, or a value obtained by normalizing the feature associated with the heart rate to a feature associated with the heart rate obtained at the time of calibration.

The first candidate feature may include a ratio between an amplitude of a reflection wave component in the bio-signal and an amplitude at a predetermined point in a systolic interval and the second candidate feature may include a ratio between the amplitude of the reflection wave component in the bio-signal and an amplitude of a propagation wave component.

The predetermined point in the systolic interval may include at least one of a maximum amplitude point and a point obtained by internally dividing a time of the propagation wave component and a time of the maximum amplitude point.

The processor may be further configured to acquire a second-order differential signal of the bio-signal and extract the first candidate feature and the second candidate feature based on a local minimum point of the second-order differential signal.

The processor may be further configured to combine the first candidate feature and the second candidate feature by using a linear combination function including an average or by using a non-linear combination function.

According to an aspect of an example embodiment, there is provided a method of estimating blood pressure, including: acquiring a bio-signal from an object; obtaining a feature for blood pressure estimation by using the bio-signal; and estimating a blood pressure by using the feature for blood pressure estimation, wherein the obtaining the feature for blood pressure estimation includes extracting a reference feature based on the bio-signal, and obtaining, as the feature for blood pressure estimation, a first candidate feature based on the reference feature being less than a first threshold; a second candidate feature based on the reference feature being greater than or equal to a second threshold that is greater than the first threshold, or a combination of the first candidate feature and the second candidate feature based on the reference feature being greater than or equal to the first threshold and less than the second threshold.

The reference feature may include at least one of a heart rate, a feature associated with the heart rate, a value obtained by normalizing the heart rate to a heart rate obtained at a time of calibration, or a value obtained by normalizing the feature associated with the heart rate to a feature associated with the heart rate obtained at the time of calibration.

The first candidate feature may include a ratio between an amplitude of a reflection wave component in the bio-signal and an amplitude at a predetermined point in a systolic interval and the second candidate feature may include a ratio between the amplitude of the reflection wave component in the bio-signal and an amplitude of a propagation wave component.

BRIEF DESCRIPTION OF THE DRAWINGS

The above and other aspects, features, and advantages of the disclosure will be more apparent from the following detailed description of example embodiments taken in conjunction with the accompanying drawings, in which.

DETAILED DESCRIPTION

Figure 1:
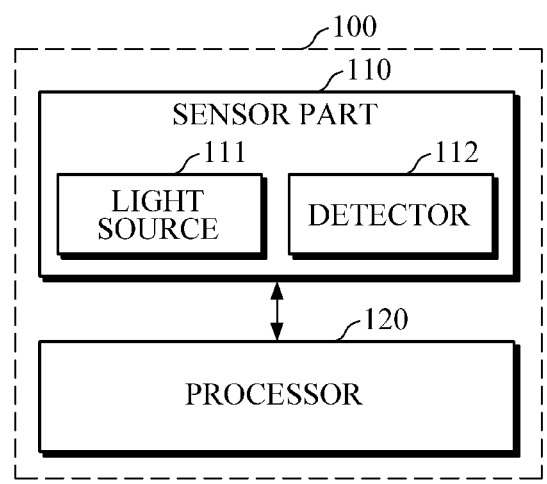
FIG. 1 is a block diagram illustrating an apparatus for estimating blood pressure according to an example embodiment.

Details of example embodiments are provided in the following detailed description with reference to the accompanying drawings. The disclosure may be understood more readily by reference to the following detailed description of example embodiments and the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience. The disclosure may, however, be embodied in many different forms and should not be construed as being limited to the embodiments set forth herein. Rather, these embodiments are provided so that the disclosure will be thorough and complete and will fully convey the concept of the invention to those skilled in the art, and the disclosure will only be defined by the appended claims. Like reference numerals refer to like elements throughout the specification.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

FIG. 1 is a block diagram illustrating an apparatus for estimating blood pressure according to an example embodiment. FIGS. 2A to 2D are diagrams for describing an example embodiment of obtaining features for blood pressure estimation.

Referring to FIG. 1, an apparatus 100 for estimating blood pressure includes a sensor part 110 and a processor 120.

The sensor part 110 acquires a bio-signal from an object and transmits the acquired bio-signal to the processor 120. The bio-signal may include various bio-signals, such as a photoplethysmogram (PPG) signal (hereinafter referred to as a "pulse wave signal"), an electrocardiography (ECG) signal, an electromyography (EMG) signal, and the like, which may be modeled by a plurality of waveform components. Hereinafter, a pulse wave signal will be described as an example.

The sensor part 110 may include a PPG sensor configured to measure a pulse wave signal. The PPG sensor may include a light source 111 configured to emit light to an object and a detector configured to detect the light that is returned after being scattered, reflected, or transmitted through a biological tissue of the object. The light source may include at least one of a light emitting diode, a laser diode, or a phosphor, but is not limited thereto. The detector may include a photodiode, a photo transistor, an image sensor (e.g., a complementary metal-oxide semiconductor (CMOS)), a spectrometer, and the like.

Upon receiving a control signal from the processor 120, the sensor part 110 may acquire a pulse wave signal from the object. The sensor part 110 may continuously measure the pulse wave signal for a predetermined period of time during which the object in contact with the sensor part 110 applies a varying pressure to the sensor part 110. The object may be an area of the human body which may be in contact with the PPG sensor, and from which pulse waves may be easily measured. For example, the object may be a region of a wrist surface adjacent to the radial artery which is an upper area of the wrist through which capillary blood or venous blood passes. In the case of measuring pulse waves on a position of the wrist over the radial artery, there may be relatively less external factors, such as the thickness of the skin tissue of the wrist, which may cause measurement errors. The radial artery is known to be a position where blood pressure may be measured more accurately than other arteries. However, the object is not limited thereto, and may be distal body portions, such as fingers and toes, which have a high density of blood vessels.

Upon receiving a request for estimating blood pressure from a user or an external device, the processor 120 may control the sensor part 110. The processor 120 may receive a bio-signal from the sensor part 110, and perform preprocessing on the bio-signal, such as filtering for removing noise from the acquired bio-signal, amplification of the bio-signal, or converting the bio-signal into a digital signal.

The processor 120 may estimate blood pressure by analyzing the received bio-signal. The processor 120 may extract features to be used for blood pressure estimation by analyzing a waveform of the received bio-signal, and estimate blood pressure using the extracted features. However, bio-information to be measured is not limited to blood pressure, and additional bio-information, such as vascular age, arterial stiffness, aortic pressure waveform, stress index, fatigue level, and the like, may be estimated.

For example, the amount of change in mean blood pressure (MAP) is known to be proportional to cardiac output (CO) and total vascular resistance (TPR) as shown in Equation 1 below.

$$\Delta MAP = CO \times TPR \qquad \text{[Equation 1]}$$

Herein, ΔMAP denotes a difference in MAP between the left ventricle and the right atrium, in which MAP of the right atrium is generally in a range of 3 mmHg to 5 mmHg, such that MAP of the right atrium is similar to MAP of the left ventricle or MAP of the upper arm. Under a condition where absolute actual CO and TPR values are known, MAP may be obtained from the aorta or the upper arm. However, it may be difficult to estimate absolute CO and TPR values based on a bio-signal. Under normal circumstances, blood pressure is regulated within the normal range. For example, when blood pressure is about to rise due to a rapid increase in cardiac output, the diameter of blood vessels relaxes so that the TPR may decrease, which may allow blood pressure to return to normal.

The processor 120 may extract a feature associated with CO (hereinafter referred to as a "CO-associated feature") and a feature associated with a TPR (hereafter referred to as a "TPR-associated feature") from the bio-signal and estimate blood pressure using the CO-associated feature and the TPR-associated feature. Here, the CO-associated feature may be a feature value that shows a tendency of increasing or decreasing proportionally to CO when the CO is relatively increased or decreased by greater than a threshold while the TPR is substantially constant as compared to a stable state. The TPR-associated feature may be a feature value that shows a tendency of increasing or decreasing proportionally to TPR when the TPR is relatively increased or decreased by greater than a threshold while the CO is substantially constant as compared to a stable state.

The processor 120 may analyze the bio-signal, a differential signal (e.g., a first order differential signal or a second-order differential signal) of the bio-signal, or the like to acquire characteristic points, for example, time and/or amplitude at the time point, and may obtain the CO-associated feature and/or the TPR-associated feature using the acquired characteristic points. For example, the processor 120 may obtain a reference feature and a plurality of candidate features using the bio-signal and progressively compare the obtained reference feature with a predefined threshold for each stage and obtain the CO-associated feature or the TPR-associated feature by combining one or two or more of the candidate features according to the comparison result of the reference feature against each threshold.

Figure 2A:
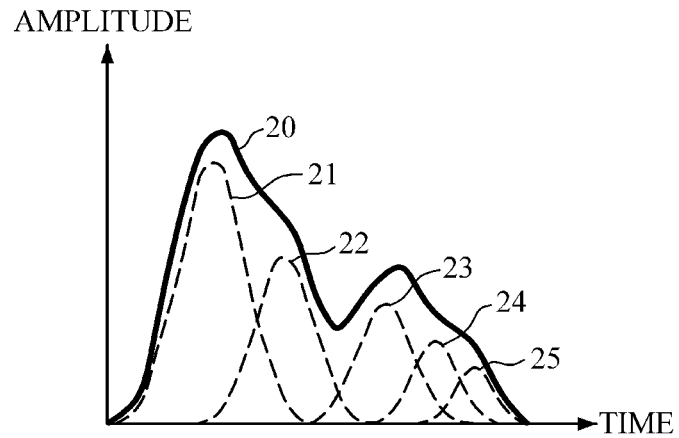
FIGS. 2A, 2B, 2C, and 2D are diagrams for describing obtaining features for blood pressure estimation according to example embodiments.

FIG. 2A is a graph illustrating an example of a pulse wave signal 20 of which a waveform is a summation of five constituent pulses 21, 22, 23, 24, and 25. A CO-associated feature and/or TPR-associated feature having high correlation with blood pressure may be extracted by using information related to each of the constituent pulses 21, 22, 23, 24, and 25 of the pulse wave signal 20. In general, constituent pulses up to the third pulse are mainly used to estimate blood pressure. Generally, finding pulses after the third pulse is difficult due to noise and they have a low correlation with estimation of the blood pressure.

Figure 2B:
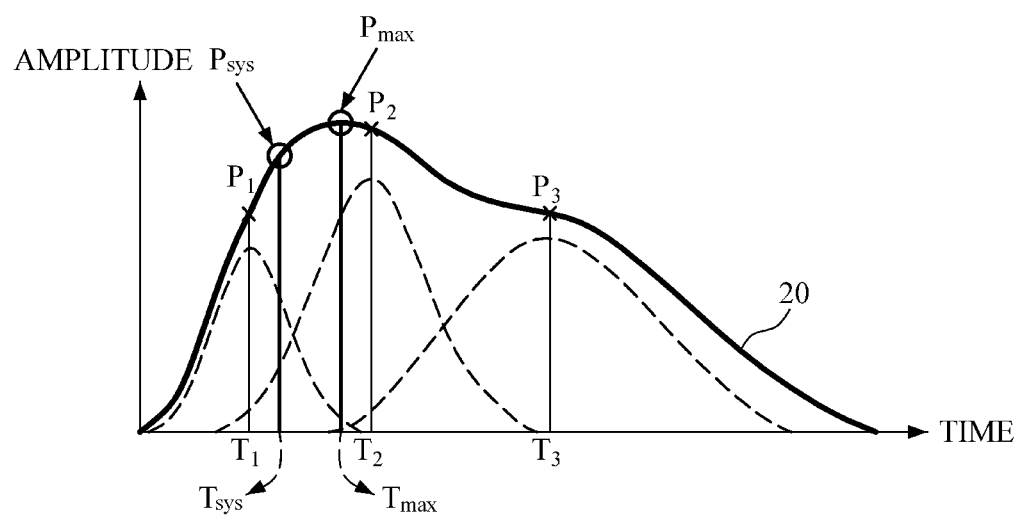
Figure 2C:
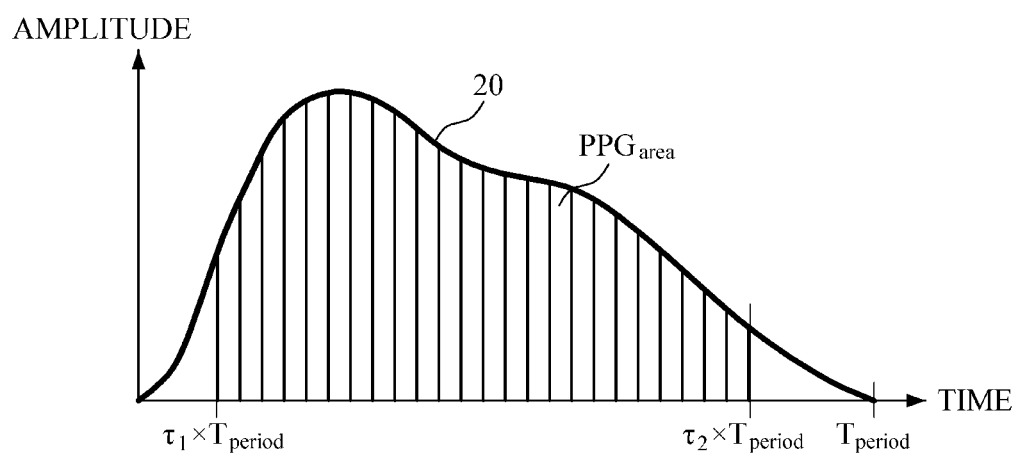

FIGS. 2B and 2C are graphs showing various characteristic points that may be acquired from a bio-signal. The characteristic points illustrated herein are merely examples and thus the embodiment is not limited thereto.

The processor 120 may extract, from a bio-signal 20 as characteristic points, a heart rate, a time $T_1$ associated with a propagation wave component and/or an amplitude corresponding to the time $T_1$, and times $T_2$ and $T_3$ associated with reflection wave components and/or amplitudes $P_2$ and $P_3$ corresponding to the times $T_2$ and $T_3$. The characteristic points associated with the propagation wave component and the reflection wave components may be extracted based on a second-order differential signal of the bio-signal. For example, a time position of the first local minimum point of a second-order differential signal may be extracted as the time $T_1$ associated with the propagation wave component and time positions of the second and third local minimum points may be extracted as times $T_2$ and $T_3$ associated with the reflection wave components. However, the embodiment is not limited thereto, and the times associated with the propagation wave component and the reflection wave components may be estimated in various manners, for example, by using times of an internally dividing point between a local minimum point and an adjacent local minimum point, an internally dividing point between a local minimum point and an adjacent local maximum point, an internally dividing point between a local maximum point and an adjacent local maximum point, and the like.

In addition, the processor 120 may extract, as the characteristic points, time and/or amplitude at a predetermined position in a systolic interval, for example, a time $T_{max}$ and/or an amplitude $P_{max}$ at a point where an amplitude has a maximum value, a time $T_{sys}$ of an internally dividing point between the time $T_{max}$ at the point where the amplitude has a maximum value and the time $T_1$ associated with the propagation wave component and/or an amplitude $P_{sys}$ corresponding to the time $T_{sys}$. The internally dividing point may be an intermediate point between two time points or a point that internally divides time between the two time points at a predetermined ratio. In addition, as shown in FIG. 2C, the area $PPG_{area}$ of the waveform of the bio-signal 20 may be extracted as a characteristic point. The area $PPG_{area}$ of the waveform of the bio-signal 20 may refer to the area of a portion of the bio-signal that is determined based on one time period $T_{period}$ of the entire bio-signal 20 and predefined arbitrary values $(\tau_1, \tau_2)$.

When the characteristic points are extracted, the processor 120 may obtain a reference feature and candidate features by using the extracted characteristic points and obtain a feature for blood pressure estimation in a stepwise manner by using the acquired reference feature and candidate features. For example, the processor 120 may progressively compare the reference feature with a first threshold and a second threshold. When the reference feature is less than the first threshold, the processor 120 may obtain a first candidate feature as a feature for blood pressure estimation, and when the reference feature is greater than or equal to the first threshold and less than the second threshold, the processor 120 may obtain a feature for blood pressure estimation by combining the first candidate feature and the second candidate feature. Otherwise, the processor 120 may obtain a second candidate feature as a feature for blood pressure estimation. The first candidate feature and the second candidate feature may be combined through arithmetic averaging, but the embodiment is not limited thereto, such that the first candidate feature and the second candidate feature may be combined using various linear combination functions including weighted averaging, or non-linear combination functions.

Figure 2D:
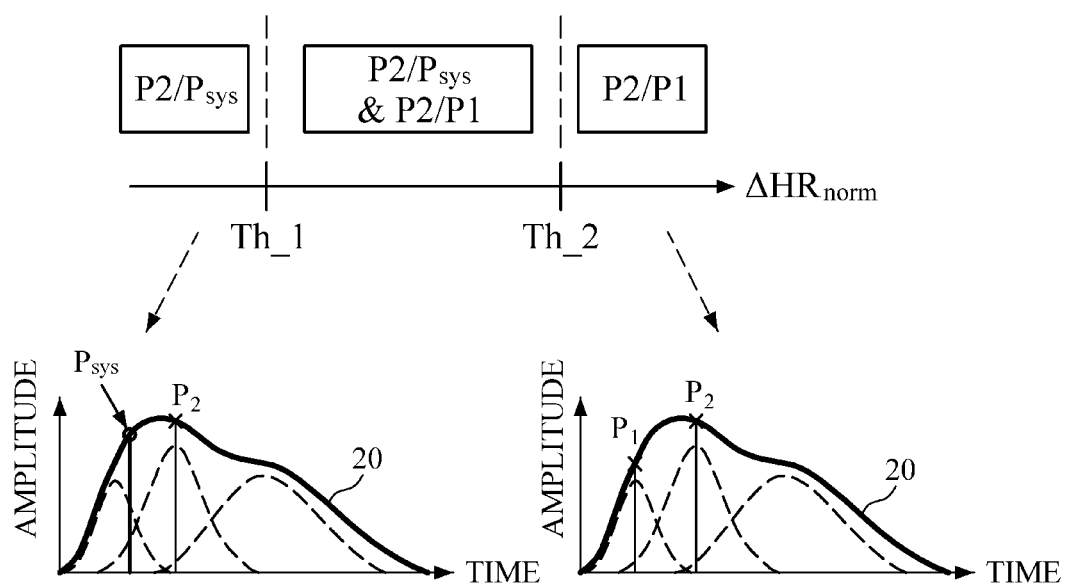

FIG. 2D is a diagram for describing an example of obtaining a TPR-associated feature among features for blood pressure estimation.

The processor 120 may obtain, as a reference feature, a heart rate, a value normalized by dividing the heart rate by a heart rate obtained at the time of calibration, a heart rate-associated feature that changes in proportion to the change in heart rate, a value normalized by dividing the heart rate-associated feature by a feature associated with the heart rate at the time of calibration, or the like. In addition, the processor 120 may extract, for example, a ratio $P_2/P_{sys}$ between an amplitude $P_2$ of a reflection wave component and an amplitude $P_{sys}$ at a predetermined point in a systolic interval as the first candidate feature, and extract a ratio $P_2/P_1$ between the amplitude $P_2$ of the reflection wave component and an amplitude $P_1$ of a propagation wave component as the second candidate feature.

The processor 120 may compare the reference feature with a preset first threshold Th_1 and obtain the first candidate feature $P_2/P_{sys}$ as a TPR-associated feature if the reference feature is less than the first threshold Th_1. If the reference feature is greater than or equal to the first threshold Th_1, the processor 120 may compare the reference feature with a second threshold Th_2 and obtain a combination of the first candidate feature $P_2/P_{sys}$ and the second candidate feature $P_2/P_1$, for example, an arithmetic average of the first candidate feature $P_2/P_{sys}$ and the second candidate feature $P_2/P_1$, as the TPR-associated feature when the reference feature is less than the second threshold. If the reference feature is greater than or equal to the second threshold Th_2, the second candidate feature $P_2/P_1$ may be obtained as the TPR-associated feature.

Although the TPR-associated feature is obtained through a two-step threshold comparison by using two candidate features of different magnitudes, the embodiment is not limited thereto. That is, two candidate features may be used to obtain features representing other blood pressure mechanisms, such as a CO-associated feature, and features representing various blood pressure mechanisms may be obtained based on more precise magnitude change through three or more candidate features and/or a greater than three-step threshold comparison. The threshold may be adjusted to a fixed value that may be universally applied to a plurality of users or a value that is personalized in consideration of individual users' characteristics.

As described above, according to the present embodiment, to obtain a feature representing a specific blood pressure mechanism, a change in the magnitude of two or more candidate features is gradually compared, rather than using any one candidate feature, thereby preventing degradation of the performance of blood pressure estimation due to a sudden change in the magnitude of the feature when blood pressure is estimated.

For example, the processor 120 may obtain the CO-associated feature by using a heart rate, one of characteristic points of the maximum amplitude of a systolic interval, the area of a bio-signal waveform, and the like, or a combination thereof. In addition, as described above, a plurality of candidate features may be extracted by using a heart rate, characteristic points of the maximum amplitude of a systolic interval and the area of a bio-signal waveform, and the like, and the CO-associated feature may be gradually obtained using the candidate features and a reference feature.

When the CO-associated feature and the TPR-associated feature are obtained, the processor 120 may estimate blood pressure using a blood pressure estimation model that defines the relationship between the obtained features and blood pressure. The blood pressure estimation model may be predefined in the form of a linear or non-linear function which defines the relationship between each of the CO-associated feature and the TPR-associated feature and blood pressure. The CO-associated feature and the TPR-associated feature may each be obtained for systolic blood pressure and diastolic blood pressure. In this way, systolic blood pressure and diastolic blood pressure may be individually estimated by using the CO-associated feature and TPR-associated feature obtained for each blood pressure.

Figure 3:
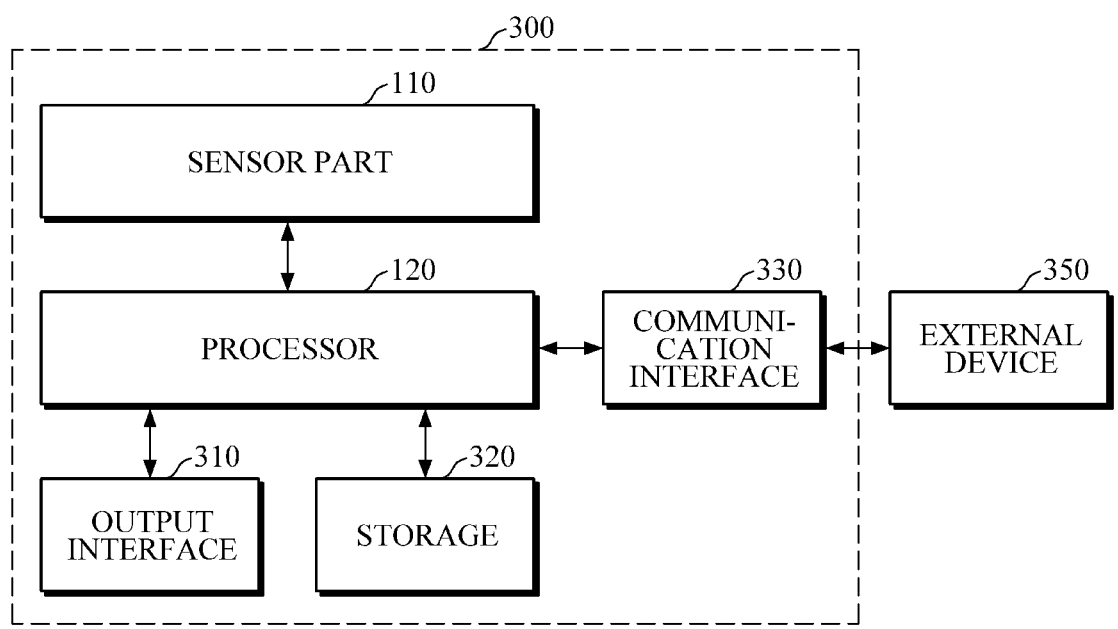
FIG. 3 is a block diagram illustrating an apparatus for estimating blood pressure according to an example embodiment.

FIG. 3 is a block diagram illustrating an apparatus for estimating blood pressure according to an example embodiment.

Referring to FIG. 3, an apparatus 300 for estimating blood pressure may include a sensor part 110, a processor 120, an output interface 310, a storage 320, and a communication interface 330.

The sensor part 110 measures a bio-signal from an object and may include a light source 111 and a detector 112 as shown in FIG. 1.

The processor 120 may obtain features representing a blood pressure mechanism, such as a CO-associated feature and a TPR-associated feature, from the bio-signal measured by the sensor part 110, and estimate blood pressure using the obtained CO-associated feature and TPR-associated feature. As described above, the processor 120 may obtain a plurality of candidate features, and obtain the CO-associated feature and/or the TPR-associated feature in a stepwise manner by using the candidate features that gradually change in magnitude.

The output interface 310 may output and provide bio-signal information measured by the sensor part 110 and various processing results of the processor 120 to a user. The output interface 310 may provide the information to the user by various visual/non-visual methods using a display module, a speaker, and/or a haptic device which are mounted in the apparatus.

For example, when the user's blood pressure is estimated, the output interface 310 may output the blood pressure using various visual methods, such as a color, a thickness of a line, a font, and the like, based on whether the estimated blood pressure falls within or outside a normal range. Alternatively, the estimated blood pressure may be output by voice or through a non-visual method in which vibration or tactile sensation is changed according to the abnormality of the blood pressure. Alternatively, when it is determined that the estimated blood pressure is abnormal when compared with the recent history of measurement, the user may be warned or advised on actions to be taken by providing, for example, cautionary food information or information on a hospital to be reserved.

The storage 320 may store reference information, the bio-signal, the obtained features, a blood pressure estimation result, and the like. The reference information may include user information, such as an age, gender, occupation, current health status, and the like, and the bio-information estimation model information, but is not limited thereto. The storage 320 may include at least one storage medium of a flash memory type memory, a hard disk type memory, a multimedia card micro type memory, a card type memory (e.g., an SD memory, an XD memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like.

In response to receiving a control signal including access information of an external device 320 from the processor, the communication interface 330 may be connected to the external device 350 by accessing a communication network through a communication technology. Once the communication interface 330 is connected to the external device 350, the communication interface 330 may receive a variety of information related to blood pressure estimation, and transmit the bio-signal measured by the sensor part 110, the blood pressure estimated by the processor 120, and the like to the external device 350. The external device 350 may include another apparatus for estimating blood pressure, a cuff-type blood pressure measurement device, a smart phone, a tablet PC, a desktop PC, a notebook PC, etc., but is not limited thereto.

Here, the communication technology may include Bluetooth communication, Bluetooth low energy (BLE) communication, near field communication (NFC), a wireless local area network (WLAN) communication, ZigBee communication, infrared data association (IrDA) communication, Wi-Fi direct (WFD) communication, ultra-wideband (UWB) communication, Ant+ communication, WiFi communication, radio frequency identification (RFID) communication, 3rd generation (3G) communication, 4G communication, 5G communication, etc., but is not limited thereto.

Figure 4:
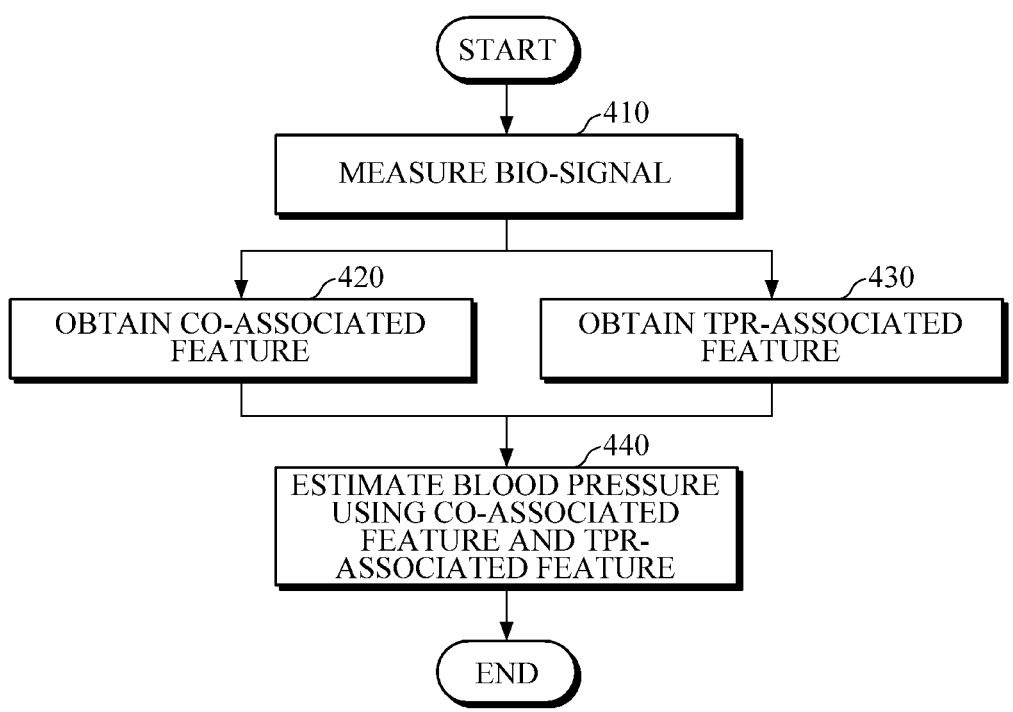
FIG. 4 is a flowchart illustrating a method of estimating blood pressure according to an example embodiment.

FIG. 4 is a flowchart illustrating a method of estimating blood pressure according to an example embodiment.

The embodiment shown in FIG. 4 may be one example of a blood pressure estimation method performed by any one of the apparatuses 100 and 200 of FIGS. 1 and 3, and thus the method will be described in brief to avoid unnecessary repetition.

First, the apparatuses 100 and 300 for estimating blood pressure may estimate a bio-signal from an object of a user upon receiving a request for estimating blood pressure in operation 410. The apparatuses 100 and 300 may receive the request for estimating blood pressure from the user through a user interface, or receive the request from an external device.

Then, a CO-associated feature may be obtained using the bio-signal in operation 420. For example, the CO-associated feature may be obtained using a heart rate, one of characteristic points of the maximum amplitude of a systolic interval and the area of a bio-signal waveform, or a combination thereof. A plurality of candidate features may be extracted by using the characteristic points, and the CO-associated feature may be gradually obtained using the candidate features and a reference feature.

In addition, a TPR-associated feature may be obtained using the bio-signal in operation 430. For example, a ratio between an amplitude associated with a propagation wave component of the bio-signal and an amplitude at a predetermined point in a systolic interval and/or a ratio between an amplitude associated with the propagation wave component and an amplitude associated with a reflection wave component may be used to obtain the TPR-associated feature. The TPR-associated feature may be obtained in a stepwise manner, as described with reference to FIGS. 5 and 6.

Then, blood pressure may be estimated using the CO-associated feature and the TPR-associated feature in operation 440. When blood pressure is estimated, information on the estimated blood pressure, for example, blood pressure estimate value, health status, warning, and actions to be taken may be provided to the user through various visual and/or non-visual methods.

Figure 5:
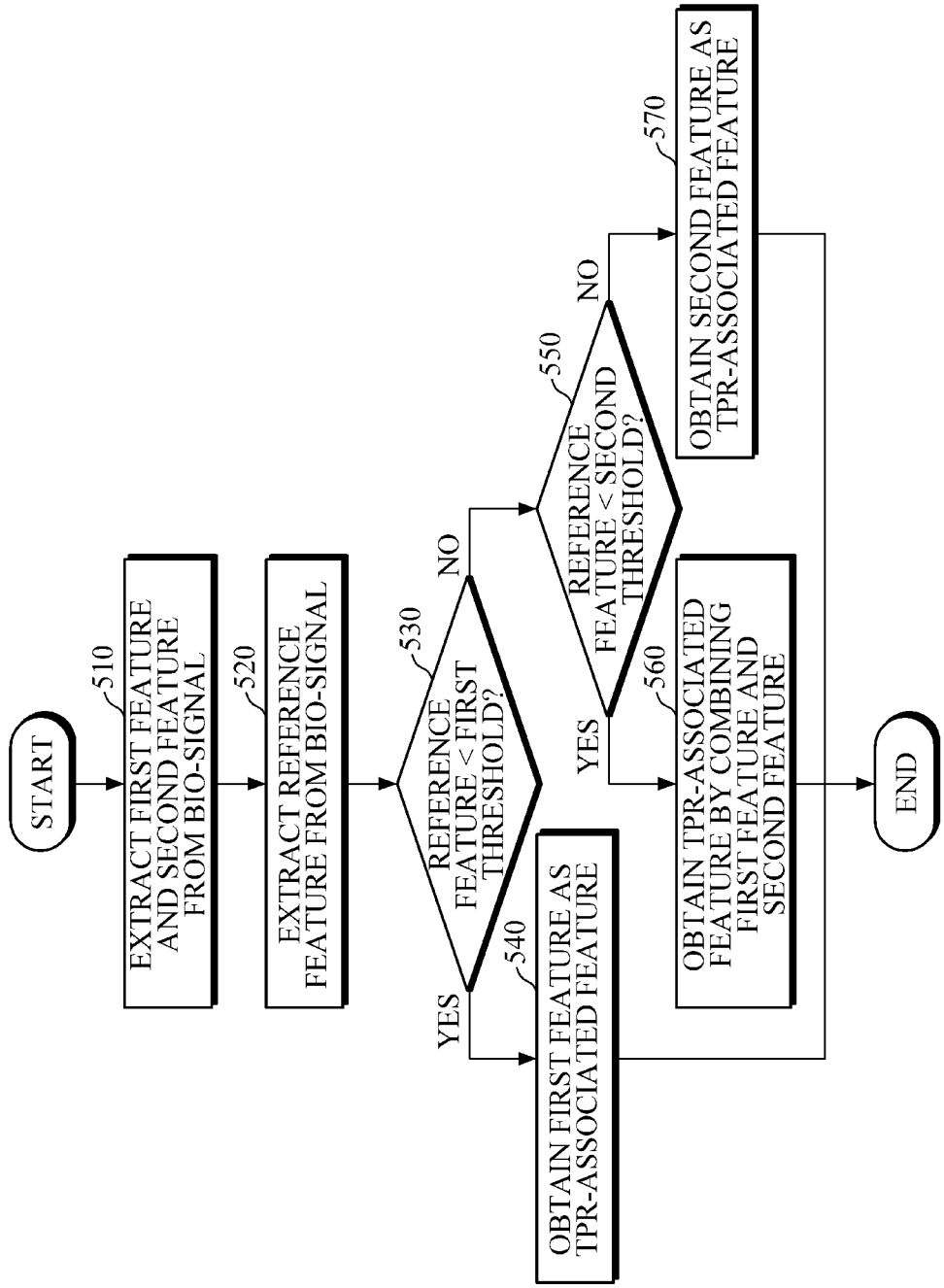
FIG. 5 is a flowchart illustrating a method of obtaining a total vascular resistance (TPR)-associated feature according to an example embodiment.

FIG. 5 is a flowchart illustrating a method of obtaining a TPR-associated feature according to an example embodiment.

FIG. 5 illustrates an example embodiment in which any one of the apparatuses 100 and 300 for estimating blood pressure obtains a TPR-associated feature among features for blood pressure estimation.

First, the apparatuses 100 and 300 for estimating blood pressure may extract a first candidate feature and a second candidate feature as TPR-associated candidate features from a bio-signal in operation 510. The first candidate feature and the second candidate feature may be extracted using the bio-signal and/or a second-order differential signal of the bio-signal. For example, a characteristic point associated with a propagation wave component and a reflection wave component may be extracted based on a local minimum point of a second-order differential signal, and candidate features may be extracted based on the extracted characteristic points. For example, a ratio between an amplitude of the reflection wave component and an amplitude at a predetermined point in a systolic interval may be extracted as a first candidate feature, and a ratio between the amplitude of the reflection wave component and an amplitude of the propagation wave component may be extracted as a second candidate feature.

Then, a reference feature may be extracted from the bio-signal in operation 520. The reference feature may be a heart rate or a value obtained by normalizing the heart rate to a heart rate obtained at the time of calibration.

Then, the reference feature may be compared with a first threshold in operation 530.

Then, if the comparison result in operation 530 shows that the reference feature is less than the first threshold, the first candidate feature is obtained as a TPR-related feature in operation 540, and otherwise, the reference feature may be compared with a second threshold in operation 550.

Then, if the reference feature is less than the second threshold in operation 550, the first candidate feature and the second candidate feature are combined to obtain a TPR-related feature in operation 560, and otherwise, the second candidate feature may be obtained as a TPR-related feature in operation 570.

Figure 6:
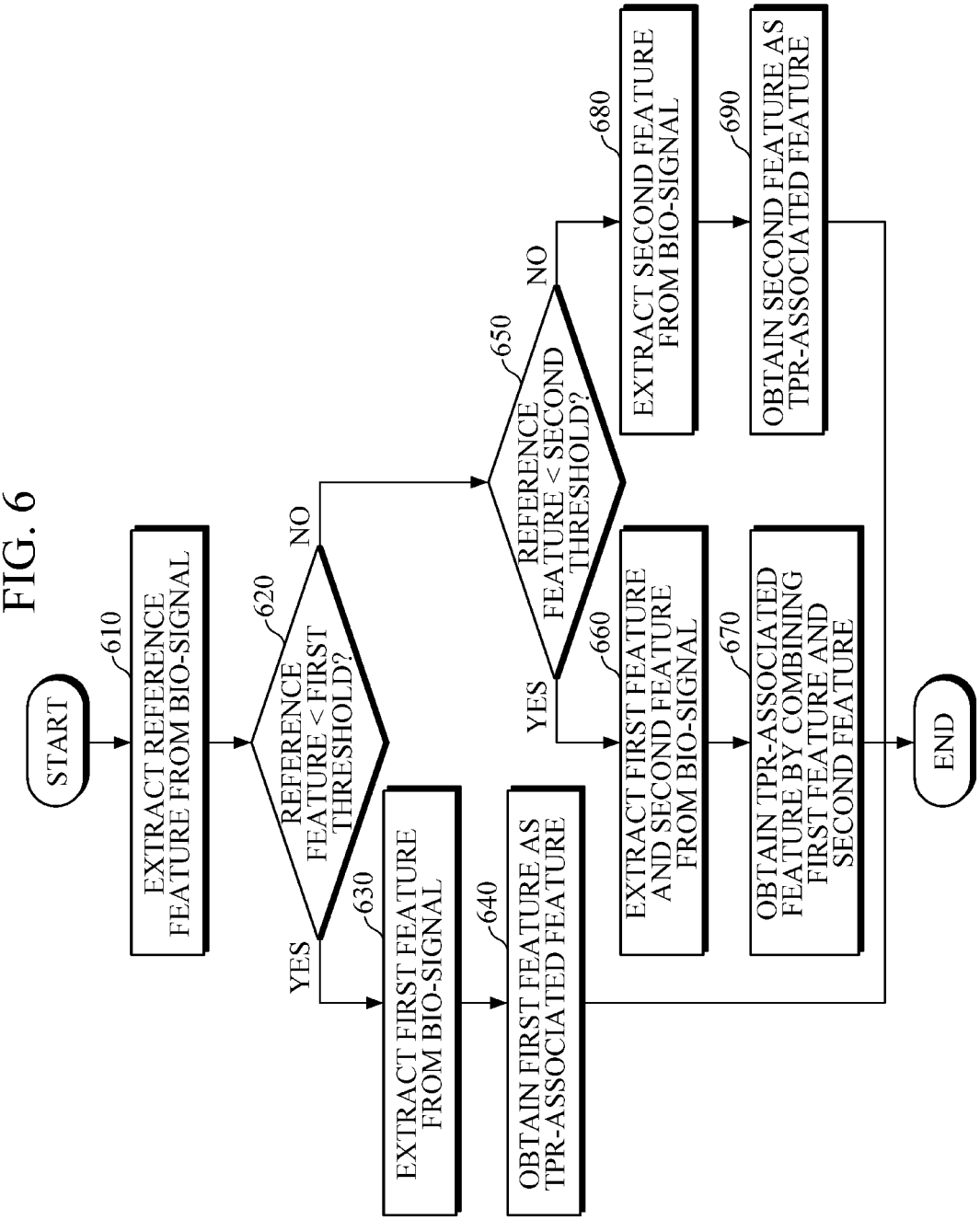
FIG. 6 is a flowchart illustrating a method of obtaining a TPR-associated feature according to an example embodiment.

FIG. 6 is a flowchart illustrating a method of obtaining a TPR-associated feature according to an example embodiment.

FIG. 6 shows an embodiment in which any one of the apparatuses 100 and 300 for estimating blood pressure obtains a TPR-related feature among features for blood pressure estimation.

First, a reference feature may be extracted from a bio-signal in operation 610. The reference feature may be a heart rate or a value obtained by normalizing the heart rate to a heart rate obtained at the time of calibration.

Then, the reference feature may be compared with a first threshold in operation 620.

Then, if the comparison result of operation 620 shows that the reference feature is less than the first threshold, a first candidate feature may be extracted in operation 630, and the extracted first candidate feature may be obtained as a TPR-associated feature in operation 640. For example, a characteristic point related to a reflection wave component may be extracted based on the second local minimum point of a second-order differential signal, and, for example, a ratio between an amplitude of the reflection wave component and an amplitude at a predetermined point in a systolic interval may be extracted as the first candidate feature.

Then, if the reference feature is equal to or greater than the first threshold in operation 620, the reference feature may be compared with a second threshold in operation 650.

Then, if the reference feature is less than the second threshold in operation 650, a first candidate feature and a second candidate feature may be extracted from the bio-signal in operation 660, and the extracted first and second candidate features are combined to obtain a TPR-associated feature in operation 670. For example, characteristic points associated, respectively, with the propagation wave component and the reflection wave component may be extracted based on the first local minimum point and the second local minimum point of the second-order differential signal, and, for example, a ratio between an amplitude of the reflection wave component and an amplitude at a predetermined point in a systolic interval may be extracted as the first candidate feature and a ratio of the amplitude of the reflection wave component and an amplitude of the propagation wave component may be extracted as the second candidate feature.

Then, if the reference feature is greater than or equal to the second threshold in operation 650, the second candidate feature may be extracted from the bio-signal in operation 680, and the extracted candidate feature may be obtained as a TPR-associated feature in operation 690. For example, characteristic points related to the propagation wave component and the reflection wave component may be extracted based on a local minimum point of the second-order differential signal, and a ratio between an amplitude of the reflection wave component and an amplitude of the propagation wave component may be extracted as the second candidate feature.

Figure 7:
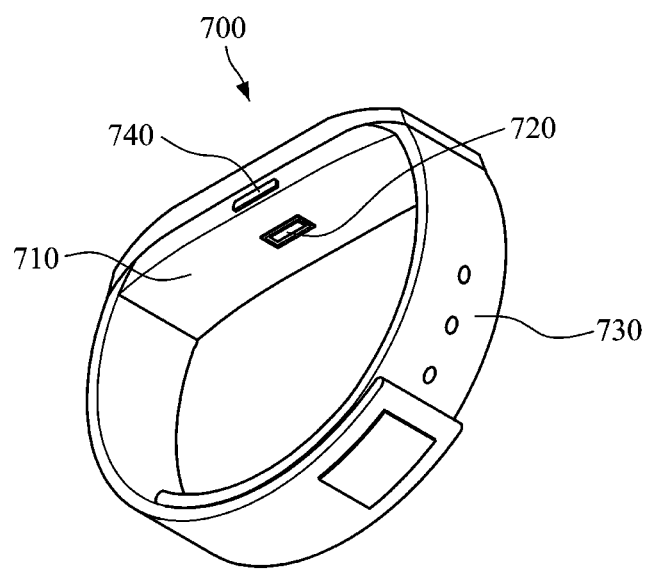
FIGS. 7, 8, and 9 are diagrams illustrating electronic devices including an apparatus for estimating blood pressure according to example embodiments.
Figure 8:
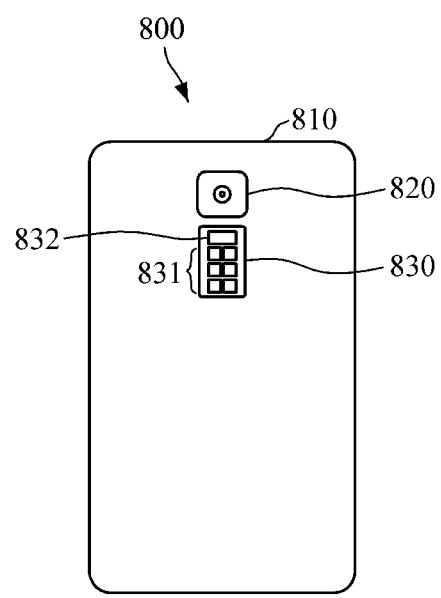
Figure 9:
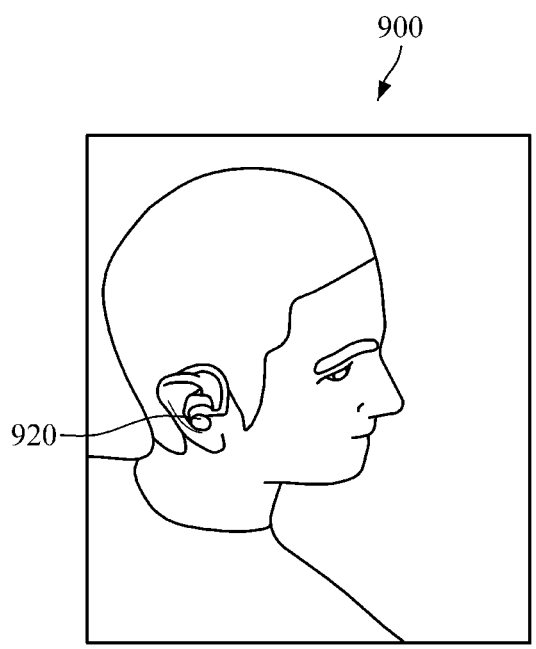

FIGS. 7 to 9 are diagrams for describing various example embodiments of an electronic device including an apparatus for estimating blood pressure.

An electronic device including the apparatus 100 or 300 for estimating blood pressure described above may include a wearable device 700 of a smart watch type, a mobile device 800, such as a smartphone, an ear-wearable device 900, and the like, as shown in FIGS. 7 to 9. However, the electronic device is not limited to the aforementioned examples, and may include a smart band, smart glasses, a smart ring, a smart patch, a smart necklace, a tablet PC, etc. The electronic device may include the apparatus 100 or 300 for estimating blood pressure and all components of the apparatus 100 or 300 may be mounted in one electronic device, or separately mounted in two or more electronic devices.

Referring to FIG. 7, the wearable device 700 of a smart watch type includes a main body 710 and a strap 730. The strap 730 may be flexible, and may be connected to both ends of the main body 710 to be bent around a user's wrist. The strap 730 may include a first strap and a second strap that are separate from each other. Each of one ends of the first strap and the second strap may be connected to each of the both ends of the main body 710, and the first strap and the second strap may be fastened to each other via fastening means. The fastening means may be formed as a magnet fastening means, a Velcro fastening means, a pin fastening means, but is not limited thereto. Air may be injected into the strap 730 or an airbag may be included in the strap 730, so that the strap 730 may have elasticity according to a change in pressure applied to the wrist, and the change in pressure of the wrist may be transmitted to the main body 710. A battery may be embedded in the main body 710 or the strap 730 to supply power to the wearable device 700.

A sensor part 720 of the apparatus 100 or 300 for estimating blood pressure may be mounted on a rear surface of the main body 710 and include a light source and a detector. The processor of the apparatus 100 or 300 for estimating blood pressure may be provided in the main body 710. The processor may be electrically connected to various components, such as the sensor part 720, to control the components, and may control and perform the aforementioned blood pressure estimation and/or various other functions of the electronic device.

In addition, a storage may be included in the main body 710 to store various types of information to be used for estimating blood pressure and/or acquiring features for blood pressure estimation and information processed by other components. Also, a manipulator 740 may be mounted on one side of the main body 710 to receive a command of the user and transmit the received command to the processor. The manipulator 740 may include a power button to input a command to turn on/off the wearable device 700.

Moreover, a display may be mounted on the front surface of the main body 710, and the display may include a touch screen enabling touch input. The display may receive a touch input of the user, transmit the touch input to the processor, and display a processing result of the processor.

In addition, a communication interface may be mounted in the main body 710 to communicate with an external device. The communication interface may transmit and receive data to and from the external device.

Referring to FIG. 8, the mobile device 800 of a smartphone type may include a main body and a display pane. The main body may form the outer appearance of the mobile device 800. The display panel and cover glass may be sequentially arranged on a first surface of the main body, and the display panel may be exposed to the outside through the cover glass. A sensor part 830 may be provided on a second surface of the main body, and the sensor part 830 may include one or more light sources 831 and a detector 832. In addition, a camera module 820 and/or an infrared sensor may be provided on the second surface of the main body. The processor and other components, such as the communication interface, the storage, and the like, of the apparatus 100 or 300 for estimating blood pressure may be provided in the main body to estimate blood pressure as described above, store a processing result, or communicate with an external device.

Referring to FIG. 9, the ear wearable device 900 may include a main body and an ear strap. The user may wear the electronic device by wearing the ear strap on the auricle. The ear strap may be included according to the type of the wearable device 900. The main body may be inserted into the external auditory meatus of the user. The main body may be equipped with a sensor part 920. The wearable device 900 may provide a blood pressure estimation result to the user as sound, or transmit the blood pressure estimation result to an external device, for example, a mobile device, a tablet device, a PC, etc., through a communication module provided in the main body.

The example embodiments may be implemented as computer readable codes in a computer readable recording medium. Codes and code segments of the computer program according to the example embodiments may be inferred by a skilled computer programmer in the art. The computer readable recording medium includes all types of recording media in which computer readable data are stored. Examples of the computer readable recording medium include a ROM, a RAM, a CD-ROM, a magnetic tape, a floppy disk, and an optical data storage. Further, the recording medium may be implemented in the form of a carrier wave such as Internet transmission. In addition, the computer readable recording medium may be distributed to computer systems over a network, in which computer readable codes may be stored and executed in a distributed manner.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

While some example embodiments have been illustrated and described above, it will be apparent to those skilled in the art that modifications and variations may be made without departing from the scope of the disclosure as defined by the appended claims and their equivalents. For example, suitable results may be achieved if the described techniques are performed in a different order and/or if components in a described system, architecture, device, or circuit are combined in a different manner and/or replaced or supplemented by other components or their equivalents.

What is claimed is:

1. A method of obtaining a feature for blood pressure estimation, the method comprising:
    extracting a reference feature from a bio-signal;
    obtaining a feature for blood pressure estimation by:
        determining, as the feature for blood pressure estimation, a first candidate feature based on the reference feature being less than a first threshold;
        determining, as the feature for blood pressure estimation, a second candidate feature based on the reference feature being greater than or equal to a second threshold that is greater than the first threshold; and
        determining, as the feature for blood pressure estimation, a combination of the first candidate feature and the second candidate feature based on the reference feature being greater than or equal to the first threshold and less than the second threshold; and
    estimating a blood pressure by using the obtained feature.

2. The method of claim 1, wherein the reference feature comprises at least one of a heart rate, a feature associated with the heart rate, a value obtained by normalizing the heart rate to a heart rate obtained at a time of calibration, or a value obtained by normalizing the feature associated with the heart rate to a feature associated with the heart rate obtained at the time of calibration.

3. The method of claim 1, wherein the first candidate feature comprises a ratio between an amplitude of a reflection wave component in the bio-signal and an amplitude of a predetermined point in a systolic interval.

4. The method of claim 3, wherein the predetermined point in the systolic interval comprises at least one of a maximum amplitude point and a point obtained by internally dividing a point corresponding to a time of a propagation wave component and a point corresponding to a time of the maximum amplitude point in a graph representing the bio-signal over time.

5. The method of claim 1, wherein the second candidate feature comprises a ratio of an amplitude of a reflection wave component and an amplitude of a propagation wave component in the bio-signal.

6. The method of claim 1, further comprising, prior to extracting the reference feature, extracting the first candidate feature and the second candidate feature based on the bio-signal.

7. The method of claim 6, wherein the extracting the first candidate feature and the second candidate feature comprises acquiring a second-order differential signal of the bio-signal and extracting the first candidate feature and the second candidate feature based on a local minimum point of the acquired second-order differential signal.

8. The method of claim 1, wherein
    the determining, as the feature for blood pressure estimation, the first candidate feature comprises extracting the first candidate feature from the bio-signal, based on the reference feature being less than the first threshold, and determining the extracted first candidate feature as the feature for blood pressure estimation;

the determining, as the feature for blood pressure estimation, the second candidate feature comprises extracting the second candidate feature from the bio-signal, based on the reference feature being greater than or equal to the second threshold, and determining the extracted second candidate feature as the feature for blood pressure estimation; and the determining, as the feature for blood pressure estimation, the combination of the first candidate feature and the second candidate feature comprises extracting the first candidate feature and the second candidate feature from the bio-signal, based on the reference feature being greater than the first threshold and less than the second threshold, obtaining the combination of the first candidate feature and the second candidate feature based on the extracted first candidate feature and the extracted second candidate feature.

9. The method of claim 1, wherein the obtaining the feature for blood pressure estimation based on the combination of the first candidate feature and the second candidate feature comprises obtaining the feature for blood pressure estimation through a linear combination or a non-linear combination of the first candidate feature and the second candidate feature.

10. An apparatus for estimating a blood pressure, the apparatus comprising:
a sensor configured to acquire a bio-signal from an object; and
a processor configured to:
extract a reference feature based on the bio-signal;
determine, as a feature for blood pressure estimation, a first candidate feature based on the reference feature being less than a first threshold; a second candidate feature based on the reference feature being greater than or equal to a second threshold that is greater than the first threshold; and a combination of the first candidate feature and the second candidate feature based on the reference feature being greater than or equal to the first threshold and less than the second threshold; and
estimate a blood pressure by using the determined feature.

11. The apparatus of claim 10, wherein the feature for blood pressure estimation comprises a cardiac output (CO)-associated feature and a total peripheral resistance (TPR)-associated feature.

12. The apparatus of claim 11, wherein the CO-associated feature comprises at least one of a heart rate, a maximum amplitude of a systolic period, or an area of a bio-signal waveform.

13. The apparatus of claim 10, wherein the reference feature comprises at least one of a heart rate, a feature associated with the heart rate, a value obtained by normalizing the heart rate to a heart rate obtained at a time of calibration, or a value obtained by normalizing the feature associated with the heart rate to a feature associated with the heart rate obtained at the time of calibration.

14. The apparatus of claim 10, wherein the first candidate feature comprises a ratio between an amplitude of a reflection wave component in the bio-signal and an amplitude at a predetermined point in a systolic interval and the second candidate feature comprises a ratio between the amplitude of the reflection wave component in the bio-signal and an amplitude of a propagation wave component.

15. The apparatus of claim 14, wherein the predetermined point in the systolic interval comprises at least one of a maximum amplitude point and a point obtained by internally dividing a point corresponding to a time of the propagation wave component and a point corresponding to a time of the maximum amplitude point in a graph representing the bio-signal over time.

16. The apparatus of claim 14, wherein the processor is further configured to acquire a second-order differential signal of the bio-signal and extract the first candidate feature and the second candidate feature based on a local minimum point of the second-order differential signal.

17. The apparatus of claim 10, wherein the processor is further configured to combine the first candidate feature and the second candidate feature by using a linear combination function including an average or by using a non-linear combination function.

18. A method of estimating a blood pressure, the method comprising:
acquiring a bio-signal from an object;
obtaining a feature for blood pressure estimation by using the bio-signal; and
estimating a blood pressure by using the obtained feature,
wherein the obtaining the feature for blood pressure estimation comprises:
extracting a reference feature based on the bio-signal; and
determining, as the feature for blood pressure estimation, a first candidate feature based on the reference feature being less than a first threshold; a second candidate feature based on the reference feature being greater than or equal to a second threshold that is greater than the first threshold; and a combination of the first candidate feature and the second candidate feature based on the reference feature being greater than or equal to the first threshold and less than the second threshold.

19. The method of claim 18, wherein the reference feature comprises at least one of a heart rate, a feature associated with the heart rate, a value obtained by normalizing the heart rate to a heart rate obtained at a time of calibration, or a value obtained by normalizing the feature associated with the heart rate to a feature associated with the heart rate obtained at the time of calibration.

20. The method of claim 18, wherein the first candidate feature comprises a ratio between an amplitude of a reflection wave component in the bio-signal and an amplitude at a predetermined point in a systolic interval and the second candidate feature comprises a ratio between the amplitude of the reflection wave component in the bio-signal and an amplitude of a propagation wave component.

\* \* \* \* \*